United States Patent [19]

Beebe et al.

[11] Patent Number: 4,705,617
[45] Date of Patent: Nov. 10, 1987

[54] APPARATUS FOR DEPLATING CUTANEOUS GAS SENSORS

[75] Inventors: Cedric H. Beebe, Fullerton; Larry S. McDavid, Anaheim; Michael Pawlowski, Chino, all of Calif.

[73] Assignee: Sensormedics Corporation, Anaheim, Calif.

[21] Appl. No.: 492,108

[22] Filed: May 6, 1983

[51] Int. Cl.⁴ .................. G01N 27/46; G12B 13/00
[52] U.S. Cl. .................. 204/402; 204/406; 204/415; 364/497; 364/571
[58] Field of Search .......... 204/415, 406, 402, 434; 128/635; 364/497, 499, 500, 571

[56] References Cited

U.S. PATENT DOCUMENTS

| | | | |
|---|---|---|---|
| 2,918,420 | 12/1959 | Sabins | 204/402 X |
| 3,523,883 | 8/1970 | Waclawik et al. | 204/402 |
| 3,616,412 | 10/1971 | Gnage | 204/402 |
| 3,788,958 | 1/1974 | Dillenberg | 204/146 |
| 3,900,375 | 8/1975 | Baboian | 204/140 |
| 4,033,830 | 7/1977 | Fletcher, III | 204/402 X |
| 4,057,478 | 11/1977 | Bruckenstein et al. | 204/402 |
| 4,077,861 | 3/1978 | Lauer | 204/402 |
| 4,090,935 | 5/1978 | Dunning, Jr. et al. | 204/146 |
| 4,197,853 | 4/1980 | Parker | 128/635 |
| 4,233,124 | 11/1980 | Tomaszewski | 204/146 |
| 4,301,807 | 11/1981 | Mentelos | 128/635 |
| 4,321,113 | 3/1982 | Grambow et al. | 204/406 X |

FOREIGN PATENT DOCUMENTS 1531761 11/1978 United Kingdom ........... 204/402
2079474 1/1982 United Kingdom ........... 204/402

OTHER PUBLICATIONS

Beran et al., "Cutaneous Blood Flow and Its Relationship to Transcutaneous $O_2/CO_2$ Measurement", Critical Care Medicine, vol. 9, No. 10, pp. 734-741 (1981).

Primary Examiner—John F. Niebling
Assistant Examiner—Nam X. Nguyen
Attorney, Agent, or Firm—Lyon & Lyon

[57] ABSTRACT

An improved method and apparatus for deplating the electrodes of cutaneous oxygen sensors. A controllable voltage source selectably establishes either a polarizing voltage or a deplating voltage between the electrodes of a cutaneous oxygen sensor, while a current sensing circuit measures the current flow therebetween. If, during the calibration of the sensor, the current flow exceeds a predetermined threshold, the apparatus initiates an operator assisted sequence of operations which deplate the electrodes and restore the gas sensor to a usable operating condition. During the performance of this sequence of operations, the apparatus carries out all steps, except those which must be performed manually by an operator.

22 Claims, 5 Drawing Figures

APPARATUS FOR DEPLATING CUTANEOUS GAS SENSORS

BACKGROUND OF THE INVENTION

The present invention relates to cutaneous gas sensors and is directed more particularly to a method and apparatus for removing the metal deposits which become plated on the electrodes of such sensors during normal operation.

Among the non-invasive patient monitoring devices which have been developed recently is an instrument known as a cutaneous gas sensor. Such gas sensors make use of known gas detection techniques to measure the partial pressure of a gas, such as oxygen or carbon dioxide, which diffuses outwardly through pores in the patient's skin. Cutaneous gas sensors have also been developed which simultaneously measure the partial pressures of both oxygen and carbon dioxide. One cutaneous gas sensor of the latter type is described in "Cutaneous Blood Flow and its Relationship to Transcutaneous $O_2/CO_2$ Measurements", by A. V. Beran, et al., "Critical Care Medicine", Vol. 9, No. 10, pages 736–741 (1981).

During operation, cutaneous gas sensors that measure oxygen tend to produce oxygen partial pressure readings which slowly increase with time. The principal reason for this increase has been found to be the plating of anode material, usually silver, onto the cathode electrode of the sensor. This plating increases the apparent oxygen partial pressure by increasing the effective area of the cathode electrode. In order to eliminate the errors that are associated with this increase, it has been the practice to visually inspect the electrodes of cutaneous gas sensors, and to clean the same when the need for deplating became apparent.

Prior to the present invention the plated anode material was commonly removed by rubbing the cathode electrode with emery paper. While this method of cleaning the cathode electrode removed the plated anode material, it often damaged the cathode electrode and surrounding structures. The use of emery paper can, for example, change the curvature of the surface of the electrode or produce flat spots thereon. Such changes in curvature or flat spots are undesirable because they tend to reduce the sensitivity of the gas sensor.

Another method that was used experimentally in an attempt to remove plated anode material prior to the present invention involved establishing a repeating sequence of deplating voltages between the anode and cathode electrodes. One such sequence included the application of $-1.2$ volts between the electrodes for four second periods at 20 second intervals, followed by the application of $+1.2$ volts for four second periods at 20 second intervals. The use of this method, however, resulted in unstable oxygen partial pressure readings and in the incomplete removal of plated anode material.

SUMMARY OF THE INVENTION

In accordance with the present invention there is provided an improved method and apparatus for deplating cutaneous gas sensors which is not subject to the above-described deficiencies.

Generally speaking the apparatus of the present invention includes circuitry for automatically detecting the presence of excessive quantities of plated material, and notifying the user of the need for deplating. When the user responds to this notification by entering a deplating command, the circuitry establishes a suitable deplating voltage between the electrodes and maintains that voltage until the deplating process is completed. The completion of the deplating process may be determined on an open loop basis by monitoring the elapse of the estimated deplating time, or on a closed loop basis by monitoring the magnitude of the deplating current.

In the preferred embodiment, the apparatus of the invention includes a digital computer which has been programmed to notify the user of the series of steps that he must perform in order to assure that the sensor is thoroughly deplated. These steps preferably include the removal of the membrane mounting assembly, the addition of a sensor deplating solution to the membrane mounting assembly and the loose reattachment of that assembly to the sensor. After the sensor has been deplated, the user is then notified of the series of steps that he must perform in order to restore the sensor to its intended operating condition. These steps preferably include the removal of the membrane mounting assembly, the rinsing and refilling of the sensor, and the attachment of a new membrane. Thus, the computer either itself performs or causes the performance of all of the steps that are necessary to restore a plated gas sensor to its intended operating condition.

By interacting with the user in the abovedescribed manner, the apparatus of the invention facilitates the practice of a new and improved method for cleaning a gas sensor. This method is calculated to assure that plated material is entirely removed from the gas sensor, rather than being simply shifted to new positions within the sensor. In addition, this method assures that the deplating process is carried to completion, independently of the skill or experience of the user. The method of the invention therefore assures that cutaneous gas sensors provide gas partial pressure data of improved accuracy and stability.

Other objects and advantages of the present invention will be apparent from the following description and drawings in which:

DESCRIPTION OF THE PREFERRED EMBODIMENTS

Figure 1:
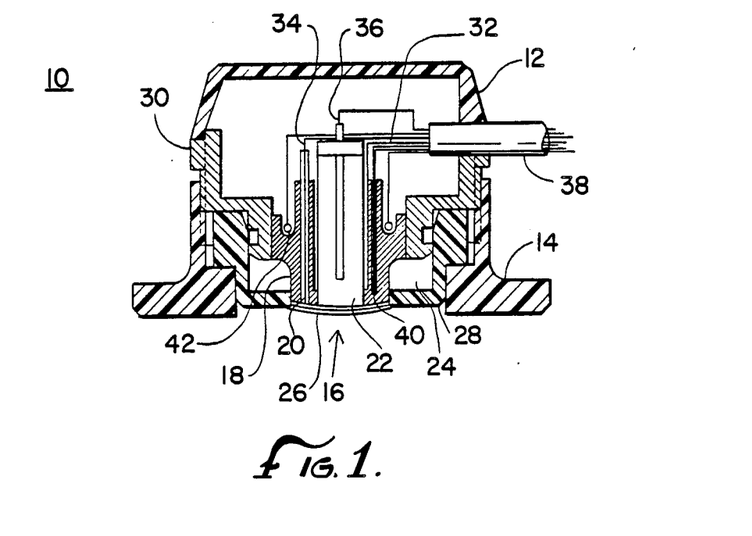
FIG. 1 is a cross-sectional view of a cutaneous gas sensor of a type which may be used with the method and apparatus of the present invention.
Figure 2:
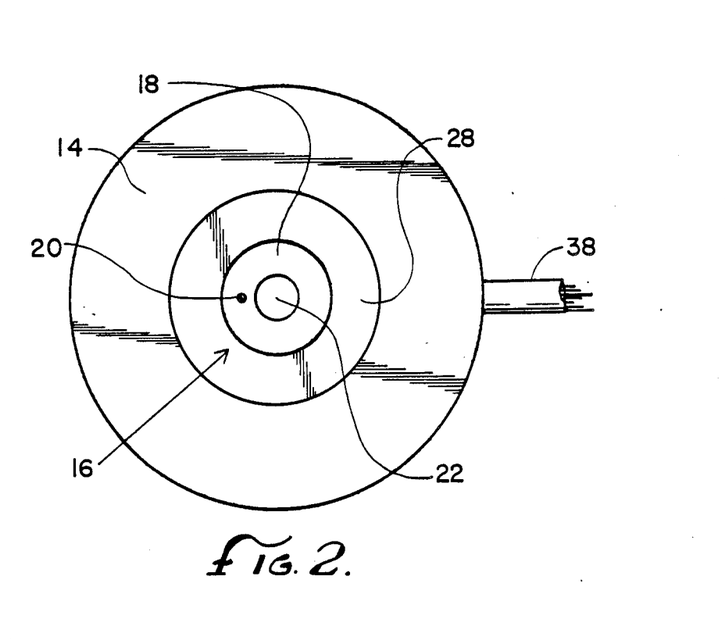
FIG. 2 is a bottom view of the gas sensor of FIG. 1.

Referring to FIG. 1, there is shown an enlarged cross-sectional view of a cutaneous gas sensor 10 of a type which is known in the art. This gas sensor includes an upper housing section 12 and a lower housing section 14, both of which are composed of a suitable plastic material. Positioned between housing sections 12 and 14 is an electrode assembly 16 which is adapted to simultaneously measure the partial pressures of oxygen and carbon dioxide. This electrode assembly includes an anode electrode 18 which is preferably composed of silver that has been coated with silver chloride, a cathode electrode 20 which is preferably composed of platinum and a glass pH electrode 22. In operation, anode electrode 18 serves as a part of an oxygen sensor that includes electrodes 18 and 20 and as a part of a carbon dioxide sensor that includes electrodes 18 and 22. The relationships between the positions, sizes and shapes of these electrodes are most easily visualized by considering FIG. 1 in conjunction with FIG. 2.

Electrode assembly 16 is mounted within gas sensor 10 by an electrically nonconductive electrode mounting member 30. This assembly is exposed to the gas to be measured through a gas permeable membrane 26 which is mounted on an electrically nonconductive membrane mounting member 28. These two mounting members are, in turn, mounted in the proper relationship to one another by virtue of their positioning between housing sections 12 and 14.

When electrode assembly 16, membrane 26 and mounting members 28 and 30 are assembled in the manner shown in FIG. 1, they define a chamber 24 which, in operation, is filled with a suitable electrolyte solution. This electrolyte solution may, for example, comprise an aqueous solution of a mixture of a soluble chloride such as potassium chloride and a soluble bicarbonate such as sodium bicarbonate. This composition is desirable because it enables the same electrolyte solution to be used both with carbon dioxide sensing electrodes 18 and 22 and with oxygen sensing electrodes 18 and 20.

Figure 3:
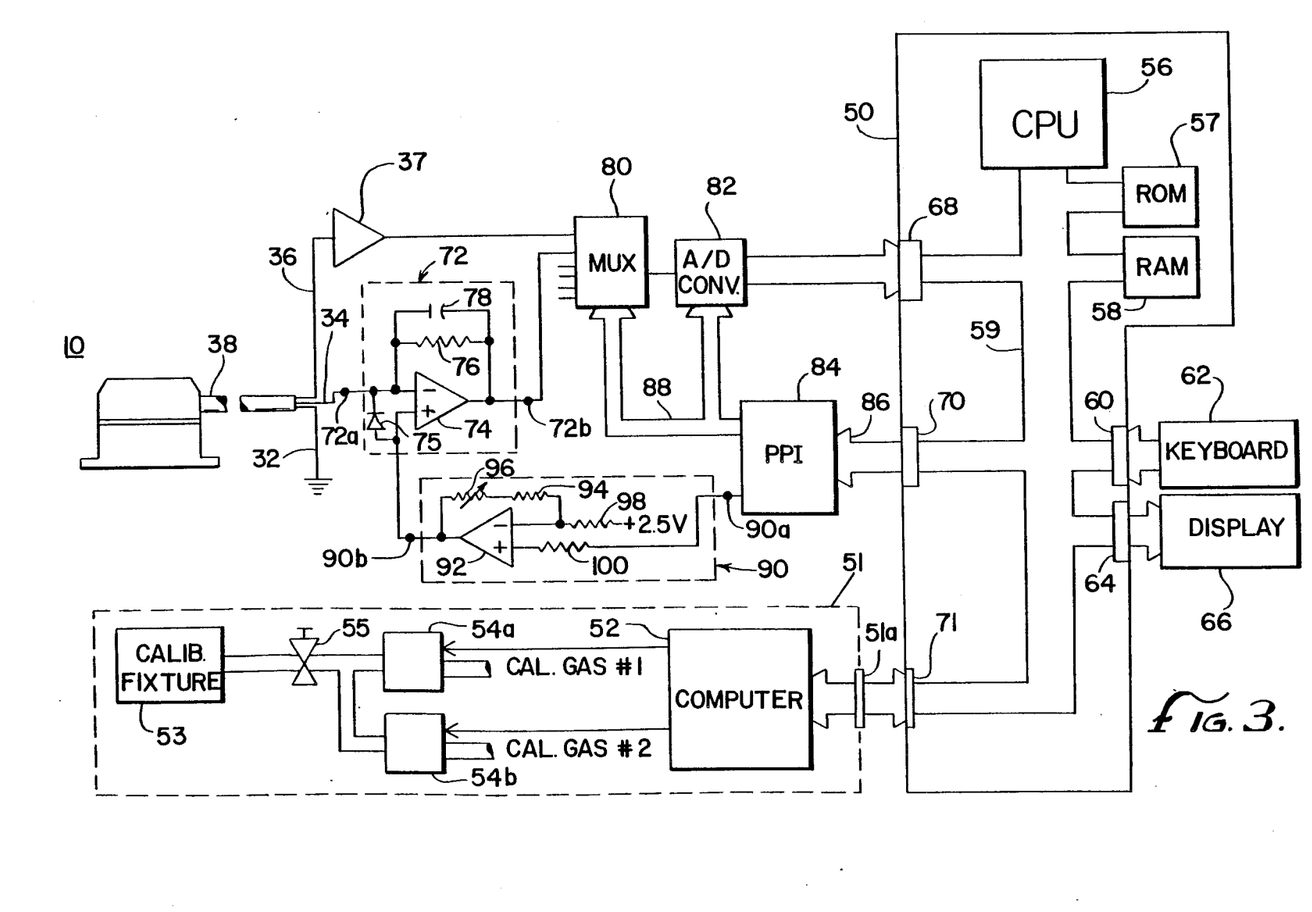
FIG. 3 is a combined block-schematic diagram of the preferred embodiment of the circuitry of the present invention.

Electrodes 18, 20 and 22 are connected to a remote instrument console, part of which is shown in FIG. 3, through respective conductors 32–36 of a suitable multiconductor cable 38. Also connected to the remote instrument console through cable 38 are the leads of a temperature sensing thermistor 40 and the leads of a heating element 42. The latter elements form a part of a closed loop temperature control circuit which maintains the operating temperature of the sensor at approximately 42° C. Because all of these parts of sensor 10 are known in the art, and form no part of the present invention, they will not be described in detail herein.

The operation of the carbon dioxide sensing portion of sensor 10 may be summarized a follows. As carbon dioxide escaping through the skin of the test subject diffuses through membrane 26, it alters the pH of the electrolyte solution in chamber 24. This change in pH is measured by electrode 22 and communicated to the remote instrument console via conductor 36. Based on this pH value the remote instrument console is able to determine the magnitude of the partial pressure of carbon dioxide in the test subject's blood.

The operation of the oxygen sensing portion of sensor 10 may be summarized as follows. During normal operation, the remote instrument console applies a polarizing voltage of approximately $-0.6$ volts from anode 18 to cathode 20. In the presence of this polarizing voltage, oxygen molecules that escape through the skin of the test subject and diffuse through membrane 26 accept electrons from cathode 20 and are reduced to hydroxyl ions. As this occurs, an equal number of electrons are released by the oxidation of the silver atoms at the surface of anode 18. Together these transfers of electrons produce a flow of current between electrodes 18 and 20. Based on the magnitude of this current, the remote instrument console is able to determine the magnitude of the partial pressure of oxygen in the test subject's blood.

Because of the reducing conditions which exist in the vicinity of cathode electrode 20, the silver ions that are dissolved in the electrolyte solution tend to become reduced as they encounter that electrode. As this occurs, silver atoms plate onto cathode electrode 20. While the low concentration of dissolved silver ions assures that this plating proceeds only very slowly, the effect of the plating is cumulative. As a result, the effective surface area of cathode electrode 20 will slowly increase with time. This increase in surface area, in turn, increases the magnitude of the current flow between electrodes 18 and 20 and thereby increases the apparent partial pressure of oxygen in the test subject's blood. Thus, the plating of anode material on cathode 20 causes an upward drift in the measured partial pressure of oxygen.

The manner in which the apparatus and method of the present invention removes the plated anode material will now be described with reference to FIGS. 3–5.

Referring to FIG. 3 there is shown a schematic-block diagram of the control circuitry for cutaneous gas sensor 10. For the sake of clarity, FIG. 3 shows only that portion of the circuitry which is associated with the application of voltages to and/or the reception of signals from electrodes 18–22, and with the communication of information between the instrument and its user.

The control circuitry shown in FIG. 3 is divided into two major parts. The first of these parts comprises a portable control unit which preferably includes a digital microcomputer 50 together with the circuits (to be described presently) which interface that computer to sensor 10. This control unit, which may be battery operated, is designed to be located close to the patient to be monitored. The second of these parts comprises a main control unit 51, which preferably also includes a digital microcomputer 52, into which the portable control unit may be plugged, via a suitable connector 51a, for calibration, battery charging and data reporting purposes. The control circuitry for sensor 10 is divided into portable and main control units solely for the convenience of the user, and has nothing to do with the present invention. Because of this, the following description will not distinguish between those activities that are controlled by computer 50, those that are controlled by computer 52, and those that are controlled jointly by both computers.

In addition to computer 52, main control unit 51 includes a calibration fixture 53 into which sensor 10 may be plugged during calibration. Once plugged into fixture 53, the sensor is supplied with one of two calibration gases from respective calibration gas tanks, not shown. The flow of these calibration gases is controlled by computer 52 via suitable solenoid operated valves 54a and 54b. The rate at which these gases flow may be controlled by a suitable manually adjustable needle valve 55. The conditions under which fixture 53 and valves 54a and 54b are used will be discussed later in connection with the flow chart of FIG. 4.

Computer 50 may comprise a conventional single board computer which includes a central processing unit or CPU 56, a program memory 57 part or all of which may be embodied in read-only memory (ROM), a random access read/write memory (RAM) 58 and a suitable data/address bus 59. Computer 50 also includes a plurality of input/output (I/O) through which it communicate with an operator or with its associated circuitry. These I/O ports include (a) a port 60 which is connected to a set of manually operable switches, such as a keyboard 62, through which the operator may enter data or commands into the computer, (b) a port 64 which is connected to a suitable human readable display 66 such as a CRT or printer through which the computer may communicate with the operator, (c) a port 68 through which the computer may receive the output signals of gas sensor 10, (d) a port 70 through which the computer may control the operation of sensor 10, and (e) a port 71 through which computer 50 may communicate with computer 52. Computer 52 will be understood to include internal circuitry which is generally similar to that of computer 50 and to have its own keyboard and display.

Lead 34 of cathode electrode 20 is connected to I/O port 68 of computer 50 through a current sensing network which preferably comprises a current-to-voltage converter network 72. The latter network includes an operational amplifier 74, a diode 75, a negative feedback resistor 76 and a filter capacitor 78. When, as is ordinarily the case, diode 75 is not conducting, network 72 serves to establish at its output 72b a voltage which is proportional to the current at its input 72a. Since the latter current is the current flowing through cathode 20, the voltage at output 72b will be proportional to the current flowing through oxygen sensing electrodes 18 and 20. Since current to voltage converter networks are well known to those skilled in the art, the operation of network 72 will not be described in detail herein.

The output voltage of sensing network 72 is applied to computer 50 through an analog multiplexer 80 and an analog to digital (A/D) converter 82. Analog multiplexer 80 may include a plurality of analog switches (not shown) through which any one of a plurality of analog signals may be applied to the input of A/D converter 82. In addition to the output signal of network 72, these analog signals may include the output signal of pH electrode 22, via conductor 36 and an amplifier 37, and the output of thermistor 40, among others. By sequentially applying these analog signals to A/D converter 82, multiplexer 80 effectively enables computer 50 to read all of the analog signals substantially simultaneously.

A/D converter 82 serves to digitize the voltages at the output of multiplexer 80 and apply them to computer 50 in multi-bit parallel form. Because the voltages which appear at the output of multiplexer 80 are all of the type which change relatively slowly with time, the input of A/D converter 82 may be connected to the output of multiplexer 80, without the usual sample and hold circuit, provided that multiplexer 80 operates slowly enough.

In order to assure that multiplexer 80 and A/D converter 82 supply data to computer 50 at the proper times, the operation thereof are controlled by computer 50 through a suitable programmable peripheral interface (PPI) network 84. The latter network, which may, for example, comprise a Model 8255 integrated circuit manufactured by National Semiconductor Corp., is connected between computer output port 70 and networks 80 and 82 through suitable multi-conductor cables 86 and 88. In operation, interface 84 serves to receive digital signals from computer 50 and format and latch the same for application to multiplexer 80 and A/D converter 82. Because the operation of such interface networks is well known, it will not be described in detail herein.

In addition to measuring the current flow between oxygen sensing electrodes 18 and 20, network 72 also serves to apply to those electrodes the voltages necessary to operate the same. These voltages are established by a voltage control network 90 which has an output 90b that is connected to the non-inverting input of amplifier 74 and to diode 75. When amplifier 74 is operating in its linear region, it is able to provide enough feedback current through resistor 76 to maintain the potential of its inverting input approximately equal to that of its non-inverting input. As a result, the potential of cathode 20 will be equal to the voltage at output 90b of voltage control network 90. Even when amplifier 74 is saturated, however, the potential of the noninverting input of amplifier 74 will be held approximately equal to that of the non-inverting input thereof by the conduction of diode 75. Thus, sensing network 72 is able to apply the output voltage of network 90 to cathode 20 under all possible circuit operating conditions.

Voltage control network 90 includes an operational amplifier 92, fixed and adjustable negative feedback resistors 94 and 96, respectively, and input resistors 98 and 100. Input resistor 98 connects the inverting input of amplifier 92 to a suitable temperature stable voltage reference that has an output voltage of, for example, +2.5 volts. Input resistor 100 connects the non-inverting input of amplifier 92 to one output of interface network 84.

When interface 84 applies a low state or ground voltage to input resistor 100, voltage control network 90 will establish the −0.6 volt polarizing voltage between cathode 20 and electrode 18. This voltage value is set in advance by adjusting the value of resistor 96. When this voltage is applied, reducing conditions will be established at cathode 20 and electrodes 18 and 20 will operate as an oxygen sensor. Under this condition, the signal which sensing network 72 applies to computer 50 will be proportional to the partial pressure of oxygen in the vicinity of sensor 10.

When, however, interface 84 applies a high state or +5 volt voltage to input resistor 100, voltage control network 90 will establish a +1.7 volt voltage from electrode 18 to cathode 20. This voltage value is set in advance by selecting the proper value for input resistor 100. When this voltage is applied, oxidizing conditions will be established at cathode 20 and electrodes 18 and 20 will operate as a deplating circuit to deplate anode material from cathode 20. Under this condition the signal which network 72 applies to computer 50 will be proportional to the magnitude of the deplating current flowing through sensor 10 until amplifier 74 saturates. After amplifier 74 saturates, deplating current will be supplied through diode 75 and the voltage at sensing network output 72b will remain at its saturation value until the deplating current becomes low enough to allow amplifier 74 to come out of saturation.

In view of the foregoing it will be seen that voltage control network 90 is adapted to apply to the oxygen sensor of sensor 10 either the polarizing voltage necessary to operate it in its measuring mode or the deplating voltage and current necessary to operate it in its deplating mode. In addition, it will be seen that the one of these voltages that is applied to the oxygen sensor is dependent solely upon the state of the digital signal which computer 50 applies to input resistor 100 through interface 84. Thus, computer 50 is able to change the operating mode of the oxygen sensor by merely changing the state of one bit of the digital signal at port 70.

Figure 4:
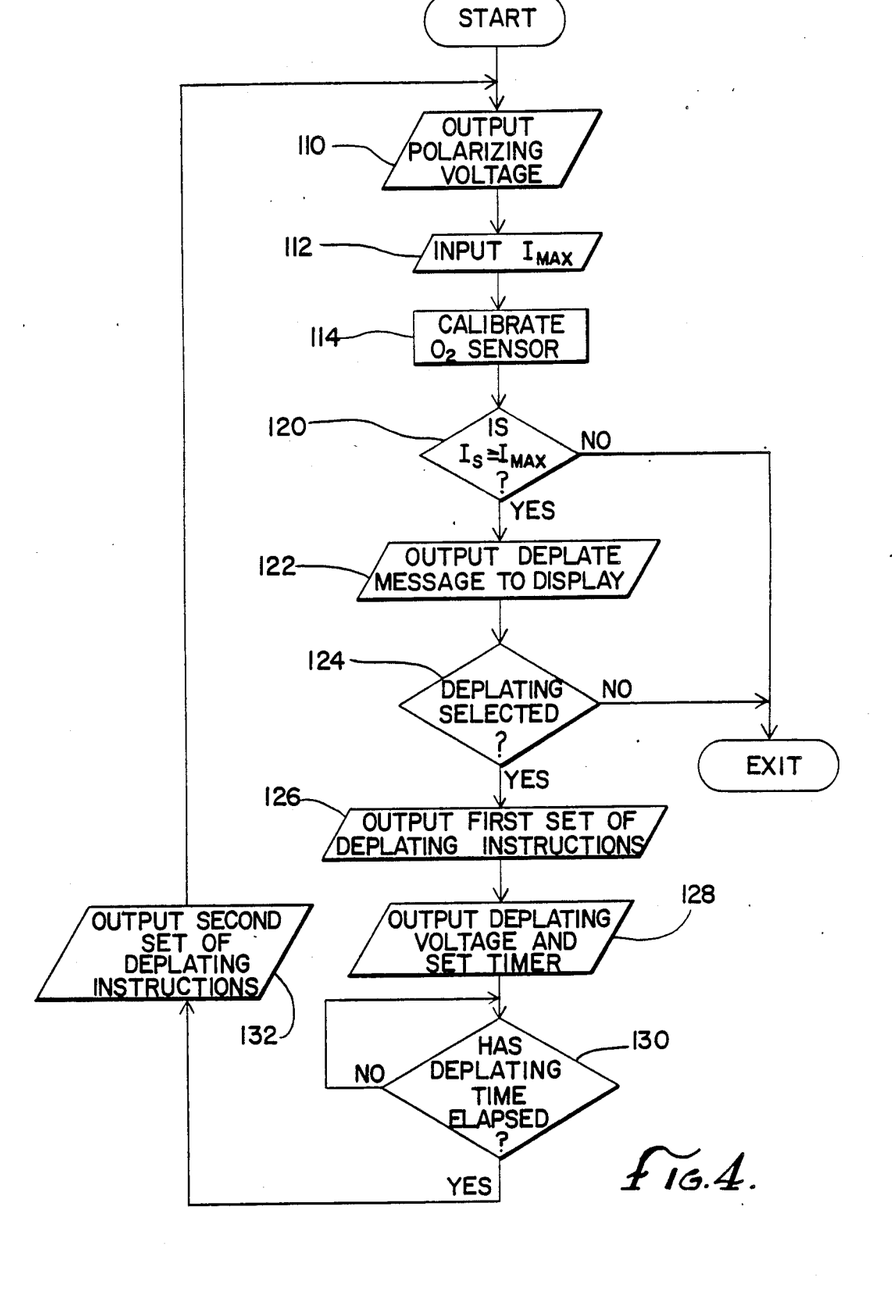
FIGS. 4 and 5 are flow charts of two different programs which may be used to control the circuitry of FIG. 3.
Figure 5:
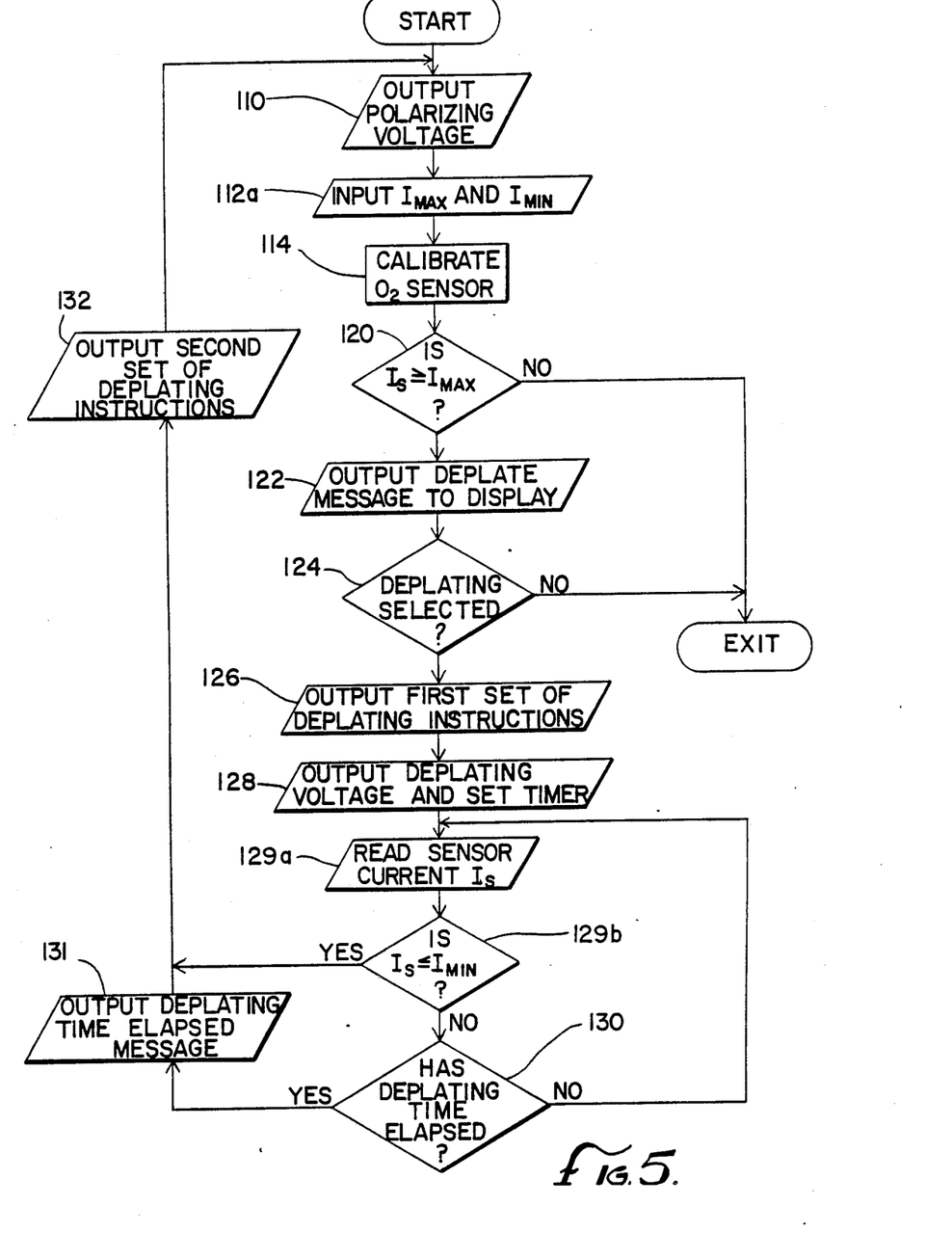

The manner in which the above-described circuitry is used to produce the results contemplated by the invention is best understood with reference to the flow charts of FIGS. 4 and 5. Referring first to FIG. 4, there is shown a flow chart of that part of the program of computers 50 and 52 which is executed before the taking of a series of oxygen partial pressure measurements. This part of the program will ordinarily be executed soon after the instrument has been turned on, initialized and warmed up to its normal operating temperature.

When the above conditions are established, the computer (50 or 52 or both) will first encounter a block 110 which causes it to apply the $-0.6$ volt polarizing voltage to the oxygen sensor. This is accomplished by applying a low state voltage to voltage control network 90 through interface 84. The computer then proceeds to a block 112 which causes it to read the value of variable $I_{max}$ from memory. The latter variable, which may be stored in ROM 57, represents a threshold current against which oxygen sensor output current $I_s$ may be compared, during calibration, to determine whether the cathode electrode is in need of deplating. (If desired, however, the computer may be programmed so that it uses as threshold current $I_{max}$ a value entered by the operator through keyboard 62.) The use of this current threshold to detect the need for deplating is possible because the concentration of oxygen in the calibration gas (e.g. 12%) is known, and because a sensor which is in need of deplating is known to produce a higher output current for a given oxygen concentration than one which is not in need of deplating.

After reading current threshold value $I_{max}$, the computer proceeds to a block 114 which causes it to calibrate the gas sensor. As this occurs, the computer will first request the operator, via display 66, to plug the active end of sensor 10 into calibration fixture 53 (see FIG. 3). Once this has been done, calibration gas will be applied to the calibration fixture through one of valves 54a and 54b. The calibration process will then proceed in a known manner, with computer 50 reading the resulting oxygen sensor output current $I_s$ through sensing network 72.

After calibration is completed, the computer proceeds to a decision block 120 which causes it to compare measured sensor current $I_s$ with current threshold $I_{max}$ to determine whether it is greater than or equal to $I_{max}$. If current $I_s$ is not greater than current $I_{max}$, it is known that the oxygen sensor does not need to be deplated. Under this condition, the computer is directed to exit the illustrated section of the flow chart and proceed with the taking of measurements.

If, on the other hand, measured sensor current $I_s$ is greater than or equal to current $I_{max}$, it is known that the oxygen sensor does need to be deplated. Under this condition the computer is directed to a block 122 which causes it to output to display 66 a message which notifies the operator of the need to deplate the sensor. After outputting this message, the computer proceeds to a decision block 124 which causes it to wait for the operator to indicate his response via keyboard 62.

If, due to time pressures or other factors, the operator does not wish to deplate the sensor, and so indicates, the computer will be directed to exit the illustrated section of the program and proceed with the taking of measurements. If, however, the operator does wish to deplate the sensor, and so indicates, the computer will be directed to a block 126 which causes it to output on display 66 a first set of deplating instructions. These instructions notify the operator of the steps which he is expected to perform to prepare the sensor for the deplating process. These steps preferably include: (1) removing the membrane mounting assembly and emptying the same, (2) adding to the mounting assembly a few drops of a suitable sensor deplating solution such as the electrolyte solution or a 0.1 molar aqueous solution of potassium chloride, and (3) reattaching the mounting assembly to the sensor so that it fits loosely thereover. Other combinations of steps will, however, accomplish substantially the same result. The steps may, for example, include: (1) removing the membrane mounting assembly, (2) inverting the sensor, i.e., placing it on a flat surface with electrode assembly 16 facing upward, and (3) placing a drop of a suitable deplating solution over cathode 20. The important thing is that the sensor be prepared for the application of the deplating voltage. It will therefore be understood that the present invention contemplates these and other combinations of steps which prepare the sensor for the application of the deplating voltage.

After requesting the performance of each of the desired steps, the computer will wait for the operator to notify it of their completion through keyboard 62. After being informed of the completion of these steps, the computer proceeds to a block 128 which causes it to apply the deplating ($+1.7$ volt) voltage to the oxygen sensor. This is accomplished by applying a high state voltage to voltage control network 90 through interface 84. The computer 50 is then directed to set a timer by entering the stored plating time into a suitable counter. This deplating time will typically be 30 seconds.

As deplating proceeds, the computer is directed to a decision block 130 which causes it to repeatedly test for the elapse of the time set aside for deplating. When the deplating time does elapse, i.e., when cathode 20 has been completely deplated, the computer is directed to a block 132 which causes it to output on display 66 a second set of deplating instructions which notify the operator of the steps he must perform in order to complete the deplating process and restore the sensor to its desired operating condition. These steps preferably include: (1) removing and discarding the old membrane mounting assembly, (2) rinsing the interior of the sensor with deionized water and drying the same with a gauze pad or lintless tissue, (3) refilling the sensor with fresh electrolyte solution, and (4) attaching a new membrane mounting assembly. Other combinations of steps may, however, be used, depending upon the steps called for by the first set of deplating instructions. If, for example, the sensor was prepared for deplating in the second of the two above-mentioned ways, the operator may: (1) rinse and dry the sensor, (2) refill the sensor with fresh electrolyte solution, and (3) attach either an entire new membrane mounting assembly or the old membrane mounting member with a new membrane. The important thing is that the deplating solution be removed and that the sensor be re-assembled for normal operation. It will therefore be understood that the present invention contemplates these and other combinations of steps which remove the deplating solution and prepare the sensor for normal operation.

After requesting the performance of the desired steps, the computer will wait for the operator to notify it of their completion through keyboard 62. After being informed of the completion of the above steps, the computer is programmed to regard the deplating process as such to be completed. Since, however, the deplated sensor must be calibrated before it can be used, the computer is directed to re-execute that part of the program which is associated with the calibration of the sensor. This is done by directing the computer to return to block 110.

Upon encountering block 110, the computer will once again cause voltage control network 90 to apply the 0.6 volt polarizing voltage to the oxygen sensor. After then inputting current value $I_{max}$ per block 112, the computer will proceed to block 114 and recalibrate the oxygen sensor in the previously described manner. Because the oxygen sensor has been deplated, the sensor current $I_s$ which flows during calibration will be less than the value $I_{max}$ that is indicative of the need for deplating. As a result, when the computer encounters decision block 120, it will be directed to the exit block, thereby skipping the deplating process. The instrument will then proceed with the taking of measurements in the manner called for by the remainder of the program.

Since the time necessary to deplate cathode 20 is dependent upon the quantity of material that is plated thereon, the deplating time established by blocks 128 and 130 of FIG. 4 is preferably made long enough to deplate the largest expected quantity of plated anode material. It will therefore often happen that the cathode electrode will be fully deplated long before the deplating time has elapsed. While the continued application of deplating voltage to the sensor after deplating is completed does not damage the sensor, it does prolong the deplating process without any compensating benefit. In order to eliminate this prolongation, the flow chart of FIG. 4 may be modified so that the deplating process is terminated as soon as the magnitude of the deplating current indicates that deplating has been completed.

One illustrative embodiment of a flow chart which utilizes the magnitude of the deplating current to terminate the deplating process is shown in FIG. 5. The flow chart of FIG. 5 is generally similar to that of FIG. 4, like functioning blocks being similarly numbered, but differs therefrom in several important respects. Firstly, FIG. 5 includes a block 112a which differs from block 112 of FIG. 4 in that it calls for the computer to input both the current value $I_{max}$ which indicates the need for deplating and the current value $I_{min}$ which indicates the completion of the deplating process.

Secondly, the flow chart of FIG. 5 includes two additional blocks 129a and 129b which are inserted between blocks 128 and 130. These additional blocks cause the computer to read sensor output current $I_s$ and compare it against current value $I_{min}$. If the latter comparison indicates that current $I_s$ is greater than current $I_{min}$, the computer will be directed to decision block 130 which causes it to continue applying the deplating voltage and reading output current $I_s$, unless the deplating time has elapsed. If, however, sensor output current $I_s$ becomes less than or equal to current $I_{min}$, or if the allotted deplating time has elapsed, the computer will be directed to block 132 which causes it to output the previously described second set of operator instructions. It will therefore be seen that the flow chart of FIG. 5 allows the deplating process to be terminated either as a result of a detected current condition or as a result of elapse of the maximum allotted deplating time.

The advantage of utilizing both a current and a time condition to terminate deplating is that doing so prevents a defective gas sensor from tying up the computer. If, for example, a sensor has an excessive leakage current, it may be impossible for sensor output current $I_s$ to become less than current $I_{min}$. This, in turn, makes it impossible for the computer to proceed to block 132. Under such a condition, the deplating process will be terminated by decision block 130, thereby releasing the computer for the performance of other tasks. When this occurs, the operator may be informed of the potential defectiveness of the sensor by means of a message such as "Deplating time elapsed", as indicated by block 131. Thus, the flow chart of FIG. 5 not only speeds up the deplating process, but also helps to identify a potentially defective gas sensor.

In view of the foregoing it will be seen that the apparatus of the present invention includes circuitry for automatically detecting the presence of excessive plated material on the electrodes of cutaneous gas sensors. In addition, the apparatus of the invention includes all of the deplating and deplating control circuitry which is necessary to accomplish the sensor deplating process. Finally, the system of the present invention provides to the operator all of the information necessary to enable him to perform the manually performable parts of the deplating process at the proper times and in the proper sequence. Together these features facilitate the maintenance of optimal measuring conditions in the gas sensor with a minimum amount of operator attention and effort.

What is claimed is:

1. A deplating apparatus for a cutaneous gas sensor of the type having a gas permeable membrane, a housing defining an electrolyte chamber for receiving an electrolyte solution, an anode electrode and a cathode electrode within the electrolyte chamber, said cathode electrode being located adjacent to the gas permeable membrane, characterized by:
   (a) voltage control means for selectably establishing first and second voltages between the anode and cathode electrodes, said first voltage having a magnitude and polarity which promotes the reduction of oxygen molecules at the cathode electrode, and said second voltage having a magnitude and polarity which promotes the deplating of anode material from the cathode electrode,
   (b) a display,
   (c) a plurality of manually operable switches,
   (d) electronic control means for controlling the deplating of the gas sensor, said electronic control means serving as means:
      (i) for detecting the presence of plated anode material on the cathode electrode and indicating said presence on the display,
      (ii) responsive to the manually operable switches for causing the voltage control means to establish said second voltage between the anode and cathode electrodes, and
      (iii) for causing the voltage control means to establish said first voltage between the anode and cathode electrodes after said plated anode material has been removed from the cathode electrode,
   (e) means for connecting the electronic control means to the voltage control means,
   (f) means for connecting the voltage control means to the gas sensor, and
   (g) means for connecting the gas sensor to the electronic control means.

2. The deplating apparatus of claim 1 in which the electronic control means causes the voltage control means to establish said second voltage for a predetermined time.

3. The deplating apparatus of claim 1 in which the means for connecting the gas sensor to the electronic control means includes a current sensing network for producing an output signal indicative of the magnitude of the current flow between the anode and cathode electrodes.

4. The deplating apparatus of claim 3 in which the electronic control means causes the voltage control means to establish said second voltage between the anode and cathode electrodes until the magnitude of the current flow between those electrodes falls below a predetermined value.

5. The deplating apparatus of claim 3 in which the electronic control means detects the presence of plated anode material by comparing the output signal of the current sensing network with a predetermined maximum value.

6. The deplating apparatus of claim 5 in which the electronic control means detects the presence of plated anode material under a condition in which a gas of known composition is applied to the gas sensor.

7. The deplating apparatus of claim 3 in which the current sensing network includes an operational amplifier, and in which the output of the voltage control means is connected to one input of that operational amplifier.

8. The deplating apparatus of claim 1 in which the voltage control means includes an operational amplifier, and in which the means for connecting the electronic control means to the voltage control means includes means for connecting the electronic control means to the operational amplifier.

9. The deplating apparatus of claim 8 in which the electronic control means applies a two-state voltage to the operational amplifier.

10. The deplating apparatus of claim 9 in which the operational amplifier is also connected to a source of a fixed voltage, and in which the output voltage of the operational amplifier is proportional to the algebraic sum of said fixed voltage and said two-state voltage.

11. The deplating apparatus of claim 1 in which the electronic control means is a computer that is programmed to output on said display a sequence of deplating instructions that notify an operator of the steps that he must perform in order to assist in the deplating of the gas sensor.

12. The deplating apparatus of claim 11 in which the computer is programmed to output a first sequence of deplating instructions on said display before the apparatus causes the voltage control means to establish said second voltage, and to output a second sequence of deplating instructions on said display before the apparatus causes the voltage control means to establish said first voltage.

13. The deplating apparatus of claim 11 in which the computer is programmed to allow the operator to direct the apparatus to not deplate the gas sensor.

14. A deplating apparatus for a cutaneous gas sensor of the type having a gas permeable membrane, a housing defining an electrolyte chamber for receiving an electrolyte solution, an anode electrode and a cathode electrode within the electrolyte chamber, said cathode electrode being located adjacent to the gas permeable membrane, characterized by:
(a) voltage control means for selectably establishing first and second voltages between the anode and cathode electrodes, said first voltage having a magnitude and polarity which promotes the reduction of oxygen molecules at the cathode electrode, and said second voltage having a magnitude and polarity which promotes the deplating of anode material from the cathode electrode,
(b) sensing means for producing an output signal indicative of the current flow between the anode and cathode electrodes,
(c) a display,
(d) a plurality of manually operable switches, and
(e) a digital computer connected to the voltage control means, the sensing means, the display and the switches, said computer being programmed to:
 (i) calibrate the gas sensor,
 (ii) compare the output signal of the sensing means to a predetermined maximum value, during calibration,
 (iii) cause the voltage control means to establish said second voltage between the anode and cathode electrodes and thereby deplate the cathode electrode, and
 (iv) cause said voltage control means to establish said first voltage between the anode and cathode electrodes after the cathode electrode has been deplated.

15. The deplating apparatus of claim 14 in which the computer is programmed to cause the voltage control means to establish the second voltage between the anode and cathode electrodes for a predetermined time.

16. The deplating apparatus of claim 14 in which the computer is programmed to cause the voltage control means to remove the second voltage from between anode and cathode electrodes when the magnitude of said output signal falls below a predetermined minimum value.

17. The deplating apparatus of claim 14 in which the computer is programmed to output on the display a sequence of instructions that inform an operator of the steps that he must perform in order to assist in the deplating of the sensor.

18. The deplating apparatus of claim 17 in which the computer is programmed to output a first sequence of deplating instructions on said display before the apparatus causes the voltage control means to establish said second voltage, and a second sequence of deplating instructions before the apparatus causes the voltage control means to establish said first voltage.

19. The deplating apparatus of claim 14 in which the computer is programmed to (i) output a deplate message on the display when said output signal exceeds said predetermined maximum value, and (ii) to allow an operator to use said switches to command the apparatus not to deplate the gas sensor.

20. The deplating apparatus of claim 14 in which the sensing means is a current to voltage converter network connected between the gas sensor and the computer.

21. The deplating apparatus of claim 20 in which the current to voltage converter network includes an operational amplifier having first and second inputs, a diode connected across said inputs, and means for connecting said diode to the output of the voltage control means.

22. The deplating apparatus of claim 14 in which the voltage control means includes an operational amplifier, means for connecting the amplifier to a first voltage source to receive a fixed voltage, means for connecting the amplifier to the computer to receive a two-state voltage, said operational amplifier serving to produce an output voltage that is proportional to the algebraic sum of said fixed voltage and said two-state voltage.

* * * * *